United States Patent [19]
Van Antwerp

[11] Patent Number: 5,882,494
[45] Date of Patent: *Mar. 16, 1999

[54] POLYURETHANE/POLYUREA COMPOSITIONS CONTAINING SILICONE FOR BIOSENSOR MEMBRANES

[75] Inventor: William P. Van Antwerp, Valencia, Calif.

[73] Assignee: MiniMed, Inc., Sylmar, Calif.

[*] Notice: This patent issued on a continued prosecution application filed under 37 CFR 1.53(d), and is subject to the twenty year patent term provisions of 35 U.S.C. 154(a)(2).

[21] Appl. No.: 519,693

[22] Filed: Aug. 28, 1995

Related U.S. Application Data

[62] Division of Ser. No. 410,775, Mar. 27, 1995, abandoned.

[51] Int. Cl.$^6$ .................................................. G01N 27/26
[52] U.S. Cl. ........................... 204/403; 528/28; 528/29; 528/41; 128/632
[58] Field of Search ........................ 204/403; 128/632; 528/28, 29, 41

[56] References Cited

U.S. PATENT DOCUMENTS

| | | | |
|---|---|---|---|
| 4,484,987 | 11/1984 | Gough | 204/1 T |
| 4,759,828 | 7/1988 | Young et al. | 204/1 T |
| 4,816,130 | 3/1989 | Karakelle et al. | 204/403 |
| 4,890,620 | 1/1990 | Gough | 128/635 |
| 4,909,908 | 3/1990 | Ross et al. | 204/1 T |
| 5,108,819 | 4/1992 | Heller et al. | 428/195 |
| 5,128,408 | 7/1992 | Tanaka et al. | 525/54.2 |
| 5,165,407 | 11/1992 | Wilson et al. | 128/635 |
| 5,214,119 | 5/1993 | Leir et al. | 528/28 |
| 5,238,732 | 8/1993 | Krishnan | 428/267 |
| 5,239,036 | 8/1993 | Krishnan | 528/28 |
| 5,239,037 | 8/1993 | Krishnan | 528/28 |
| 5,284,140 | 2/1994 | Allen et al. | 128/634 |
| 5,322,063 | 6/1994 | Allen et al. | 128/635 |

FOREIGN PATENT DOCUMENTS

| | | |
|---|---|---|
| 0192237 | 12/1985 | European Pat. Off. . |
| 0390390 | 3/1990 | European Pat. Off. . |
| WO/9615443 | 5/1996 | WIPO . |
| WO/9630431 | 10/1996 | WIPO . |

OTHER PUBLICATIONS

Bergveld, et al., *Advances in Biosensors*, Supplement 1, pp. 31–94.
Bindra, et al., *Anal. Chem.*, 63:1692–1696 (1991).
Fischer, et al., *Biomed. Biochim. Acta*, 48($^{11}/_{12}$):965–971 (1989).
Shaw, et al., *Biosensors & Bioelectronics*, 6:401–406 (1991).
Shichiri, et al., *Horm. Metab. Res., Supp. Ser.*, 20:17–20 (1988).
*Industrial Chemical Thesaurus*, vol. 1: *Chemical to Tradename Reference*, 2nd Edition, 1992, pp. 452 and 453.

*Primary Examiner*—Melvyn I. Marquis
*Attorney, Agent, or Firm*—Townsend and Townsend and Crew LLP

[57] ABSTRACT

A homogenous polymer composition useful as a membrane for biosensors is disclosed. The polymer composition comprises the reaction products of a diisocyanate, a hydrophilic diol or diamine, and a silicone material. An aliphatic diol or diamine may also be included. Membranes prepared from the composition allow for increasing oxygen permeability and decreased analyte permeability (e.g. glucose). They also possess the necessary physical properties of an outer polymeric biosensor membrane.

7 Claims, 7 Drawing Sheets

FIG. 1.

O=C=N-R-N=C=O     DIISOCYANATE

R= (CH$_2$)$_6$     HEXAMETHYLENE DIISOCYANATE

ISOPHORONE DIISOCYANATE 4,4'-METHYLENEBIS
(CYCLOHEXYL ISOCYANATE)

*FIG. 2.*

GENERIC BIFUNCTIONAL TERMINATED SILOXANE

AMINOPROPYLDIMETHYL TERMINATED SILOXANE

CARBOXYPROPYLDIMETHOXY TERMINATED SILOXANE

CARBINOL TERMINATED SILOXANE

*FIG. 3.*

$H(OCH_2CH_2)_nOH$     POLYETHYLENE GLYCOL $H(OCH(CH_3)CH_2)_nOH$     POLYPROPYLENE GLYCOL $NH_2CH_2CH_2(OCH_2CH_2)_nOCH_2CH_2NH_2$     AMINO PEG $$NH_2CH_2\overset{O}{\overset{\|}{C}}(OCH_2CH_2)_n O\overset{\|}{\underset{O}{C}}CH_2NH_2 \quad \text{PEG GLYCINE ESTER}$$

$$HO[CH_2CH_2O]_a[\overset{CH_3}{\overset{|}{C}HCH_2O}]_b[CH_2CH_2O]_cH \quad \text{PEG PPG BLOCK COPOLYMERS}$$
                                                                          PLURONIC AND GENAPOL

FIG. 4.

$HOCH_2CH_2OH$     ETHYLENE GLYCOL $$CH_3\underset{\underset{OH}{|}}{C}HCH_2OH \quad \text{PROPYLENE GLYCOL}$$

$HOCH_2CH_2CH_2OH$     1-3 PROPANE DIOL $H_2NCH_2CH_2CH_2NH_2$     1-3 DIAMINO PROPANE

POLYURETHANE/POLYUREA COMPOSITIONS CONTAINING SILICONE FOR BIOSENSOR MEMBRANES

This is a division, of application Ser. No. 08/410,775, filed Mar. 27, 1995 now abandoned.

FIELD OF THE INVENTION

This invention relates generally to biosensor materials. More specifically, this invention relates to a novel polymeric material that is useful as an outer biocompatible membrane for use in biosensor applications.

BACKGROUND OF THE INVENTION

Biosensors are devices that use biological (cells, enzymes, tissues etc.) to convert a chemical concentration in a matrix into a detectable signal (electrical, acoustic, optical, thermal etc.). There are many types of biosensors used for a wide variety of analytes. Electroenzymatic biosensors which use enzymes to convert a concentration to an electrical signal have been the most studied types of biosensors. For a review of some of the operating principles of biosensors, see P. Bergveld, and D. Thevenot, *Advances in Biosensors*, Supplement 1, p. 31–94, A. P. F. Turner, editor.

The prototype biosensor is the amperometric glucose sensor. There are several reasons for the wide ranging interest in glucose sensors. The scientific interest is driven by the availability of a very robust enzyme, glucose oxidase, which is used to monitor glucose, as well as the desire to develop model sensors for a wide variety of analytes. The commercial interest is driven by the need for glucose monitoring of patients with diabetes mellitus as well as the development of sensors that can be used to monitor fermentation reactions in the biotechnology arena. A working glucose sensor is also the most difficult component in development of a closed loop artificial pancreas with an implanted insulin pump.

Any amperometric glucose sensor or any oxido-reductase enzyme that uses $O_2$ as a co-substrate that is designed for subcutaneous or intravenous use requires an outer membrane and an anti-interference membrane because of the fundamental nature of the sensor and the environment in which the measurement is made.

A glucose sensor works according to the following chemical reaction (Equation 1):

In this reaction, glucose reacts with oxygen in the presence of glucose oxidase (GOX) to form gluconolactone and hydrogen peroxide. The gluconolactone reacts with water to open the lactone ring and produce produce gluconic acid. The $H_2O_2$ reacts electrochemically as shown below (Equation 2):

$$H_2O_2 \rightarrow O_2 + 2e^- 2H^+.$$

The current measured by the sensor/potentiostat (+0.5 to +0.7 V oxidation at Pt black electrode) is due to the two electrons generated by the oxidation of the $H_2O_2$. Alternatively, one can measure the decrease in the oxygen by amperometric measurement (−0.5 to −1 V reduction at Pt black electrode).

The stoichiometry of Equation 1 clearly demonstrates some of the problems with an implantable glucose sensor. If there is excess oxygen for Equation 1, then the $H_2O_2$ is stoichiometrically related to the amount of glucose that reacts at the enzyme. In this case, the ultimate current is also proportional to the amount of glucose that reacts with the enzyme. If there is insufficient oxygen for all of the glucose to react with the enzyme, then the current will be proportional to the oxygen concentration, not the glucose concentration. For the sensor to be a true glucose sensor, glucose must be the limiting reagent, i.e. the $O_2$ concentration must be in excess for all potential glucose concentrations. This means that a way must be devised to either increase the $O_2$ in the GOX membrane, decrease the glucose concentration, or devise a sensor that does not use $O_2$.

The basic problem in the use of a biosensor in the body is that the ratio of glucose to $O_2$ is opposite to what is desired for optimal operation of the biosensor. The glucose concentration in the body of a diabetic patient can vary from 2 to 30 mM (millimoles per liter or 36 to 540 mg/dl), whereas the typical oxygen concentration in the tissue is 0.02 to 0.2 mM, U. Fischer, A. Hidde, H. vonWoedtke, K. Rebrin, and P. Abel, *Biomed. Biochim. Acta.*, 1989, Vol. 48, pp. 965–971. This ratio in the body means that the sensor would be running in the Michaelis Menten limited regime and would be very insensitive to small changes in the glucose concentration. This problem has been called the "oxygen deficit problem".

Several approaches to solving the deficit problem have been attempted in the past. The simplest approach is to make a membrane that is fully $O_2$ permeable, with no glucose permeability and mechanically perforate it with a small hole that allows glucose to pass. Here the differential permeability is defined by the ratio of the small hole area to the total membrane area. Two significant problems with this method are first that reproducibly making small holes is difficult and second and more serious, the $O_2$ permeability is a strong function of the thickness of the membrane and thickness is difficult to control in mass production. Microporous membranes (U.S. Pat. No. 4,759,828 to Young et al.) have also been tried with limited success. Another problem with both the hole in the membrane approach and the microporous membrane approach is that the sensor electrodes and the enzyme layer are exposed to body fluids. Body fluids contain proteins that coat the electrodes leading to decreased sensitivity of the sensor and enzymes (proteases) that can digest or degrade the sensor active enzyme.

One approach to the oxygen deficit problem is described by Gough (U.S. Pat. No. 4,484,987).

The approach uses a combination membrane with discrete domains of a hydrophilic material embedded in a hydrophobic membrane. In this case, the membrane is not homogenous and manufacturing reproducibility is difficult. Physical properties of the membrane are also compromised. In a similar manner, Gough (U.S. Pat. No. 4,890,620) describes a "two dimensional" system where glucose diffusion is limited to one dimension while the oxygen diffusion is from both dimensions. This sensor is extremely complicated and manufacturing on a large scale is expected to be difficult.

Several other groups, G. W. Shaw, D. J. Claremont and J. C. Pickup, *Biosensors and Bioelectronics*, 1991, Vol. 6, pp. 401–406; D. S. Bindra, Y. Zhang, G. S. Wilson, R. Sternberg, D. R. Thevenot, D. Moatti and G. Reach, *Analytical Chemistry*, 1991, Vol. 63, p. 1692; and M. Shichiri, Y.

Yamasaki, K. Nao, M. Sekiya and N. Ueda, *Horm. Metab. Res., Suppl. Ser.*, 1988, Vol. 20, p. 17, have used a homogenous membrane of a relatively hydrophobic polyurethane and reported good results. In classical diffusion experiments with these membranes, however, the glucose diffusion is extremely small. It is believed that the ability of these polyurethane layers to allow glucose diffusion is due to micro cracks or micro holes in these materials when applied as membranes.

In order to circumvent the oxygen deficit problem with a homogenous membrane, Allen et al. developed two homogenous membranes with both hydrophilic and hydrophobic regions. In U.S. Pat. No. 5,284,140, they describe an acrylic system and in U.S. Pat. No. 5,322,063 they describe a polyurethane system. Both of the membranes have hydrophilic and hydrophobic moieties in the molecule leading to limited control of oxygen and glucose permeabilities.

The key to stable, high sensitivity enzyme biosensors is that the sensor output must be limited only by the analyte of interest, not by any co-substrates or kinetically controlled parameters such as diffusion. In order to maximize the output current (equation 2) of the biosensor, oxygen diffusion should be as large as possible while maintaining oxygen excess at the reaction surface. Since the normal concentration of $O_2$ in the subcutaneous tissue is quite low, maximization of the $O_2$ diffusion coefficient is desirable.

The membrane systems described in the literature as cited above attempt only to circumvent the oxygen deficit problem by reducing the amount of glucose diffusion to the working electrode of the biosensor. The magnitude of the signal from a typical biosensor of the appropriate size for either subcutaneous or intravenous implantation is typically 1 to 10 nA at physiological glucose and $O_2$ concentrations. This level of current requires sophisticated electronics for measurement. Increasing the oxygen transport and concomitant glucose transport will increase the signal and (to a limited extent) reduce the complexity of the controlling and recording electronics. It is obvious however that a membrane that simultaneously increased the oxygen and limited the glucose would lead to both better performance and increased signal.

Accordingly, there has been a need for a polymer useful in an outer polymeric membrane of a biosensor. There is a need for the membrane to have physical stability and strength, adhesion to the substrate, processibility (ability to be synthesized/manufactured in reasonable quantities and at reasonable prices), biocompatibility, ability to be cut by laser ablation (or some other large scale processing method), and compatibility with the enzyme as deposited on the sensor. The present invention fulfills these needs and provides other related advantages.

SUMMARY OF THE INVENTION

The homogenous polymer composition of the invention is fabricated from the reaction products of at least one diisocyanate, at least one hydrophilic diol or diamine, and at least one silicone material. The composition may also contain at least one short chain aliphatic diamine and/or diol. This polymer composition is useful as an outer biocompatible membrane for use in biosensors. The membranes thus formed allow for increasing oxygen permeability and decreased analyte (e.g. glucose) permeability. They also possess the necessary properties for an outer polymeric membrane.

Other features and advantages of the present invention will become apparent from the following more detailed description taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
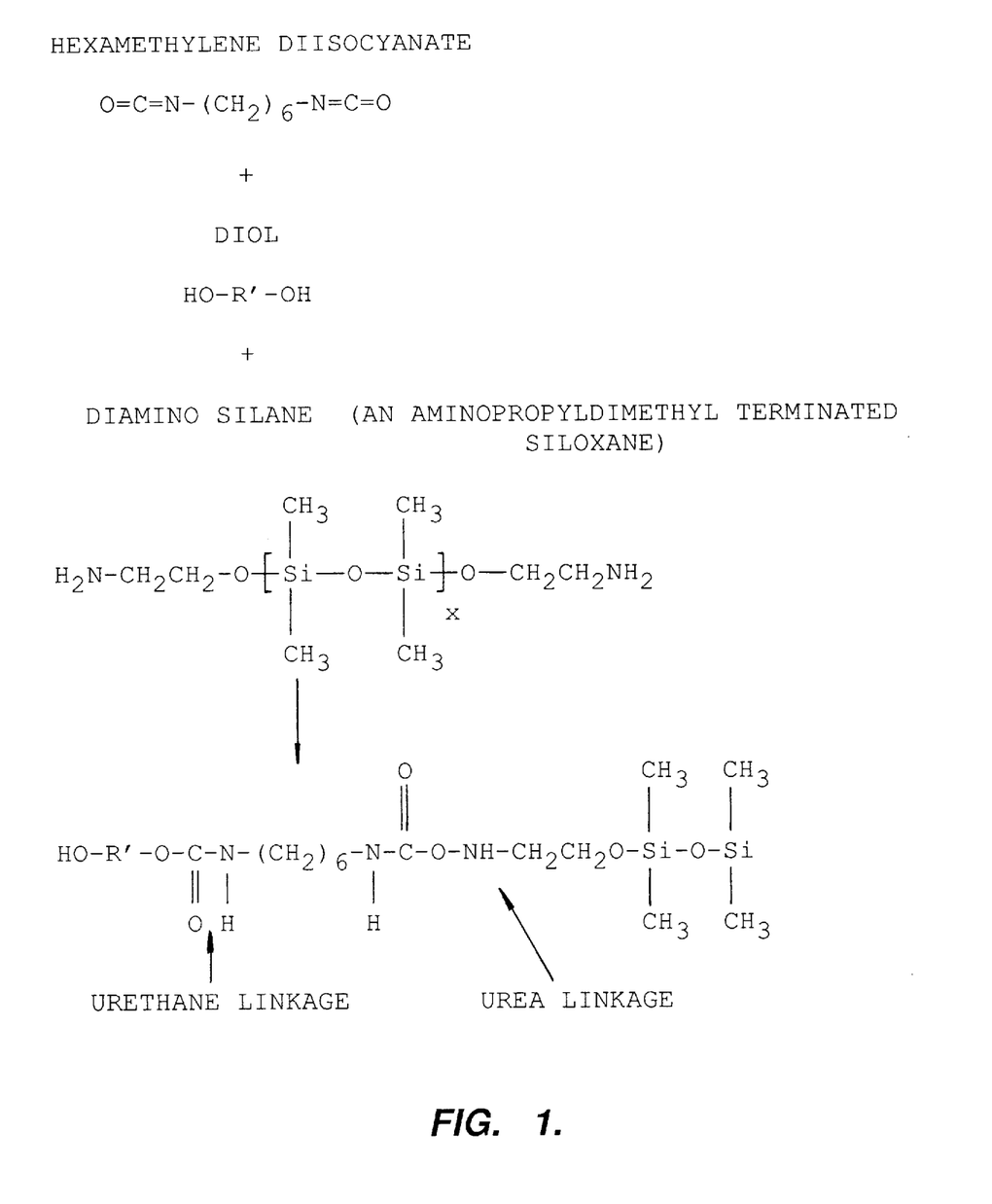
FIG. 1 shows the polymerization reaction of a diisocyanate and a diol to make a urethane linkage and the reaction of the diisocyanate and a diamine to make a urea linkage.

In a preferred embodiment, the proposed membrane for the sensor incorporates two different types of bonds and components into a single polymer. The type of polymer is a polyurethane polyurea. The chemistry of the polymerization is shown in FIG. 1 in a simplistic manner. The reactions shown in FIG. 1 show the reaction of a diisocyanate and a diol to make a urethane linkage and the same isocyanate reacting with a diamine to make a urea linkage. In alternative embodiments, the polymer may contain either the urea or the urethane linkage depending on the individual components used.

Figure 2:
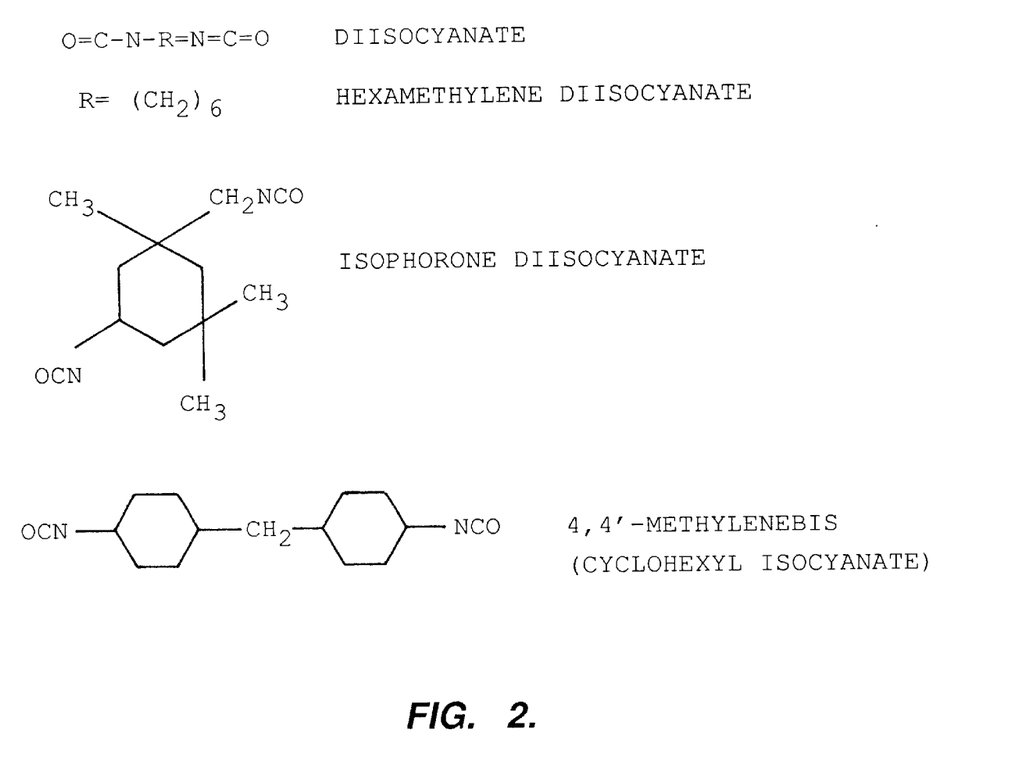
FIG. 2 shows exemplary diisocyanates used as a first component in a polymer composition of the present invention.

The polymer composition described in this invention is synthesized from three or four individual components. The basic building blocks for attachment are the exemplary diisocyanates shown in FIG. 2. These are the preferred diisocyanates for the membranes of this invention, however aromatic diisocyanates can be used if appropriate care is used to remove all of the toxic monomer from the final polymer.

Figure 3:
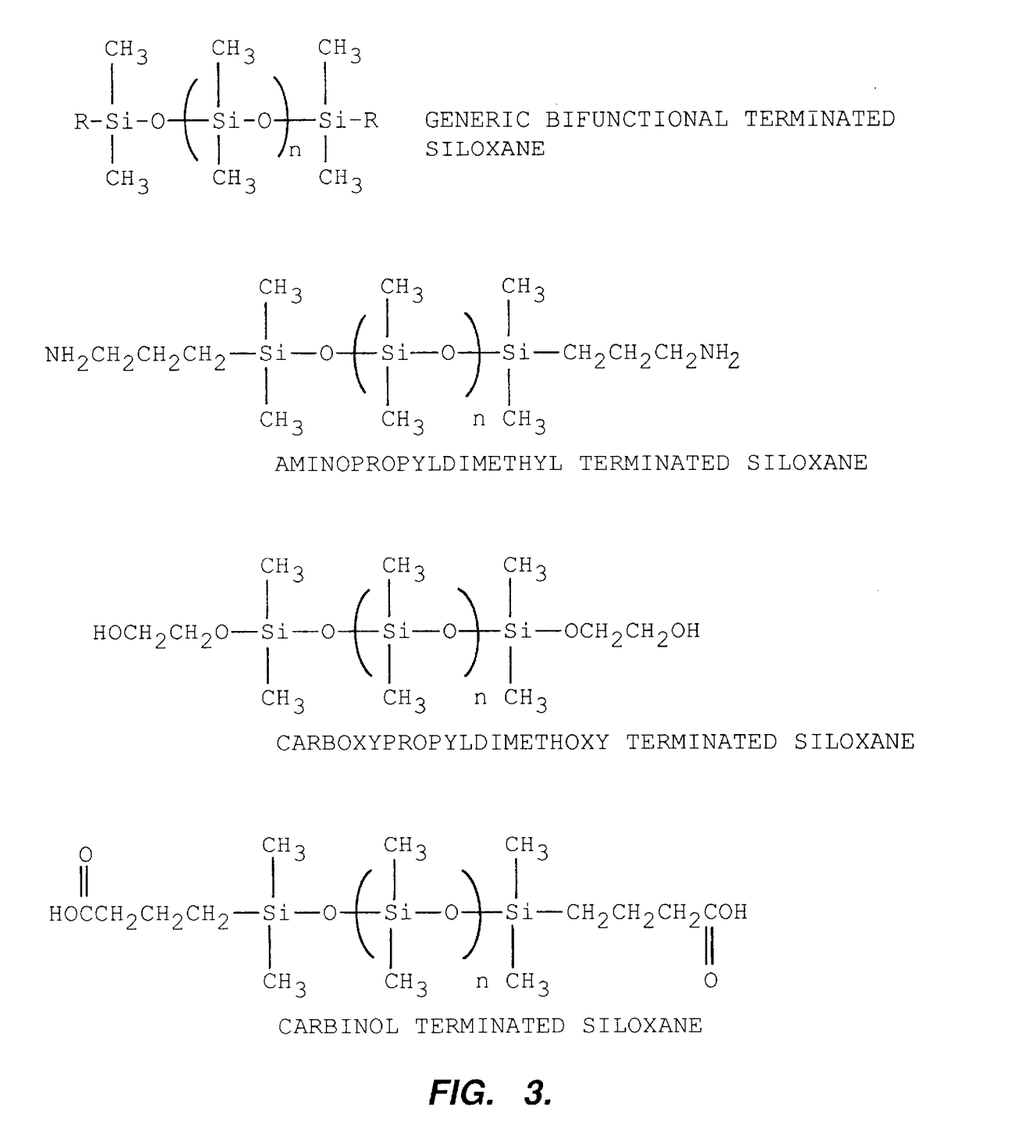
FIG. 3 shows exemplary silicones used as a second component in the polymer composition of the present invention.

Two other components are used for the final membrane polymer. The first is a silicone material (siloxane) that has excellent $O_2$ permeability. These siloxanes do not have $H_2O$ permeability so that they do not allow any glucose diffusion. A polydimethyl siloxane polymer with reactive endgroups is the preferred constituent of the polymer. FIG. 3 shows some of the potential siloxanes that have been incorporated into biosensor membranes.

Figure 4:
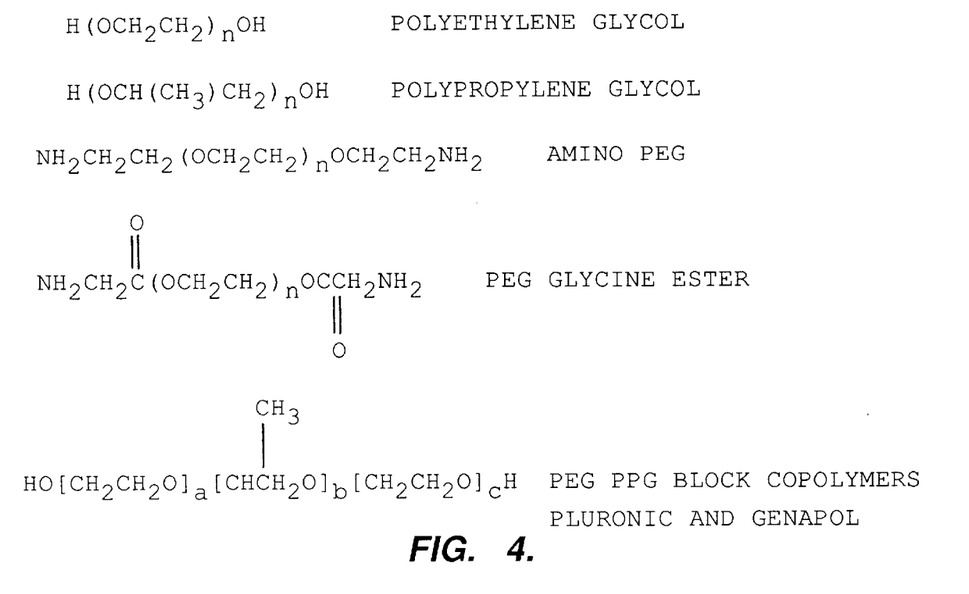
FIG. 4 shows exemplary long chain hydrophilic diols and diamines used as a third component in the polymer composition of the present invention.

Another component of the polyurethane/polyurea polymer composition is a long chain hydrophilic diol or diamine that incorporates water permeability into the polymer. Several water permeable diols and diamines have been used in the membranes and are shown in FIG. 4. These include diols like polyethylene glycol (PEG) or polypropylene glycol (PPG) and diamines of the same type. Of course, anyone skilled in the art realizes that many other diol or diamines could be substituted.

In the preliminary data, the diol used is PEG 400 or PEG 600 which is very hydrophilic and leads to good $H_2O$ transport. For the diamine a silicone material can be used. Of course, the silicone material could be a diol as well, but stable diol terminated silicones are not readily commercially available.

The silicone has excellent $O_2$ transport while the diol can be tailored to control the $H_2O$ transport and hence the glucose permeability. The use of silicone can easily increase the $O_2$ transport by a factor of five, increasing the maximal glucose permeability by 5 fold as well. Since the biosensors as constructed are kinetically limited, it is difficult to predict the exact increase in currents generated by the sensors.

Figure 5:
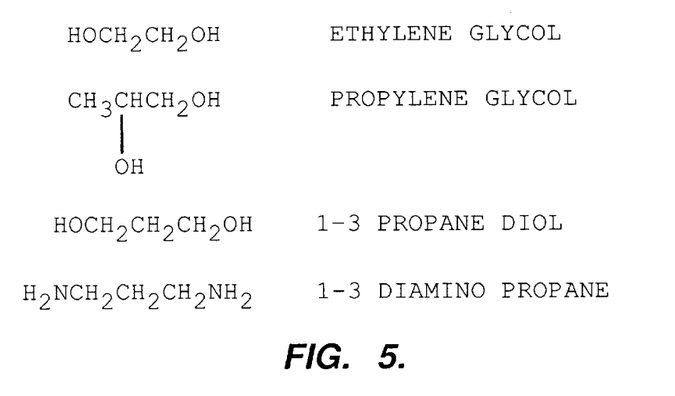
FIG. 5 shows exemplary short chain aliphatic diols and diamines that may be used in the polymer composition of the present invention.

It is sometimes necessary when synthesizing a polyurethane material to incorporate a short chain diol or diamines that would lend physical strength to the polymer but not increase its basic glucose permeability. In these cases, the diols and diamines shown in FIG. 5 have been used. Other short chain aliphatic diamines and diols could easily be substituted by one skilled in the art.

Since the siloxanes have excellent oxygen permeability and no glucose permeability, the short chain diols and diamines have fair oxygen permeability with no glucose permeability, and the long chain diols and diamines have excellent glucose permeability and good oxygen permeability, the final polymer can easily be tailored to a specific ratio of oxygen to glucose permeability. Although the ratio is the most important variable for proper glucose sensor operation, the magnitudes of the diffusion coefficients are also important since the magnitudes of the individual diffusion coefficients determine the final currents produced by a sensor and the higher the currents the easier are the electronics.

Polymerization was carried out in either solution or by bulk polymerization. In all cases, there are equal molar quantities of the diisocyanate on the one hand and the combination of the diol+diamine+short chain aliphatic diol or diamine on the other. Solution polymerization was carried out in either dimethyformamide (DMF) or tetrahydrofuran (THF).

Since water is reactive with the diisocyanates and can lead to shorter chain polymers than is optimal, precautions were taken to ensure that all solvents, reactants and glassware were as dry as possible. Short and long chain diols and long chain diamines were dried by azeotropic distillation from toluene. Aliphatic diamines were distilled from molecular sieves. Solvents were dried by distillation from CaH or molecular sieves as appropriate. Glassware was flame dried after assembly and before introduction of the reactants. Diisocyanates and siloxanes were used as received or stored over molecular sieves.

Polymerization of polyurethane/polyureas can be carried out without catalyst but in the preferred embodiment, dibutyltin bis(2-ethylhexanoate) is added in trace amounts. Bulk polymerization was usually started at about 50 degrees Celsius and when all components were mixed together, an exotherm reaction was observed to about 95 degrees Celsius in the flask. After the initial exotherm reaction, the temperature was maintained at 60 degrees Celsius to 80 degrees Celsius for about 4 hours.

Solution polymerization was carried out the same way, with the exotherm reaction only rising to 75 degrees Celsius. Solution polymerization was carried out for 12 hours (overnight) at between 50 degrees Celsius and 75 degrees Celsius.

After polymerization was complete, the reaction mixture was transferred to a large volume (5 liters or more) of rapidly stirred DI (deionized) water. The polymer that precipitated in the water was cut in small pieces and dried at 50 degrees Celsius to a constant weight.

In order that those skilled in the art can more fully understand this invention, the following examples are set forth. These examples are given solely for purposes of illustration, and should not be considered as expressing limitations unless so set forth in the appended claims. All parts and percentages are by weight, unless otherwise stated.

EXAMPLE 1

Bulk Polymerization 4.44 grams (30 mmole, 100 mole %) of isophorone diisocyanate dried over molecular sieves were transferred to a 100 ml round bottom flask fitted with a nitrogen purge line and reflux condensor. 2.40 grams (4 mmole, 20 mole %) of PEG 600 dried via toluene distillation, 1.06 grams (10 mmole 50 mole %) of diethylene glycol dried via toluene distillation and 15 grams (6 mmole, 30 mole %) of aminopropyl terminated polydimethyl siloxane MW 2500 were added to the flask. Heating via heating mantle was started until 50 degrees Celsius was obtained. At this point about 15 mg of dibutyltin bis(2-ethylhexanoate) was added to the flask and the temperature rose to about 95 degrees Celsius. The solution was stirred continuously. The solution was then heated at 65 degrees Celsius for 4 hours during which time it became increasingly viscous. The polymer was dissolved in 50 ml of hot THF and the solution was allowed to cool. After cooling, the entire solution was poured into 5 liters of stirring DI water. The precipitated polymer was torn into small pieces and dried at 50 degrees Celsius until constant weight.

EXAMPLE 2

Solution Polymerization 1.34 grams (8 mmole, 100 mole %) of dried 1,6 hexamethylene diisocyanate were added to a 100 ml 3 neck flask containing 20 ml of dry THF. 0.8 grams (4 mmole, 50 mole %) of dried PEG 200 were added with stirring. 10 grams (4 mmole, 50 mole %) of aminopropyl terminated polydimethyl siloxane MW 2500 were added. Heating via heating mantle was started until 50 degrees Celsius was obtained. At this point about 15 mg of dibutyltin bis(2-ethylhexanoate) were added to the flask and the temperature rose to about 83 degrees Celsius. The mixture was heated at 70 degrees Celsius for 12 hours and cooled. During heating the solution became very viscous, enough to stop the mechanical stirrer. The cooled solution was poured into three liters of rapidly stirred DI water and the precipitated polymer was washed with DI water three times, torn into small pieces and dried at 50 degrees Celsius until constant weight.

Membranes for testing purposes were cast several ways. In some cases, membranes were cast from THF or DMF/$CH_2Cl_2$ (2/98 vol. %) onto glass plates using a parallel arm Gardner knife. The dried films were removed, hydrated fully and their thickness measured with a micromber. In other cases, films were cast from solution onto filtration membranes of known thickness. It is assumed in the measurements reported below that the membrane material completely filled the pores of the filtration membranes and that the thickness of the filtration media is the thickness of the membrane.

Figure 6:
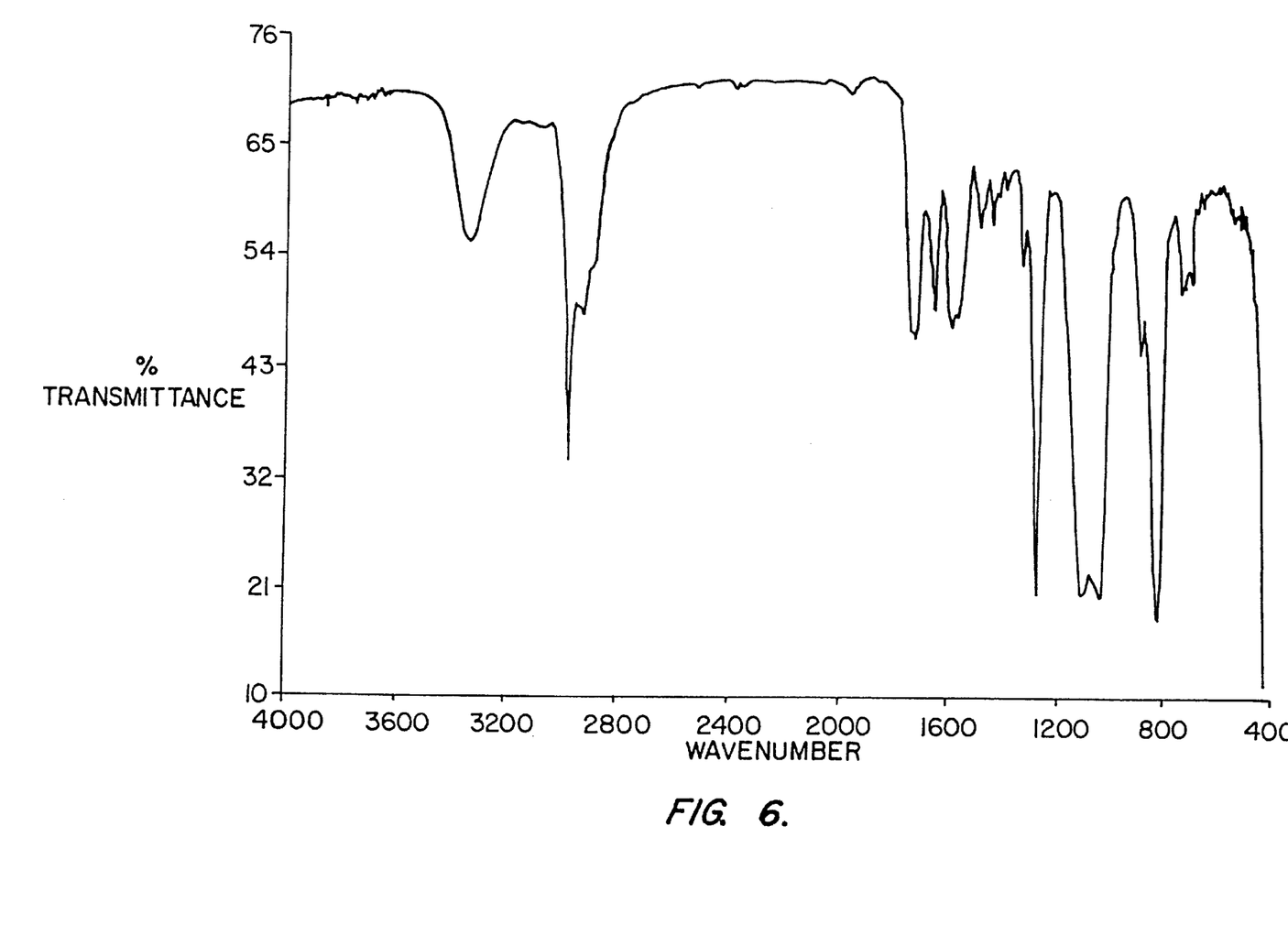
FIG. 6 shows an infrared spectrum of an exemplary polyurea composition of the present invention.

An infrared spectrum of the product of Example 2 showing the expected bands is shown in FIG. 6.

Water pickup was measured gravimetrically, Diffusion coefficients were measured using Fick's first law of diffusion in a standard permeability cell (Crown Glass Co.) at 37±0.2 degrees Celsius. The mathematics of diffusion are beyond the scope of this document however a brief outline is appropriate.

Flux=−D dc/dx is the basic diffusion equation. Here D is the diffusion coefficient which is a physical property of both the solute and the material in which it is diffusing. In other words, D is not a property of a molecule or polymer, but is a property of the system so the system needs to be fully described for the measurement to be put in context. dc/dx is the concentration gradient, dc, over the thickness of the membrane, dx. The minus sign simply denotes that the diffusion is toward the region of lower concentration. If mass balance is considered, Fick's second law of diffusion may be generated, $dc/dt = D\ d^2c/dx^2$. By assuming Dirichlet boundary conditions, this equation can be solved using Laplace transform techniques.

The oxygen diffusion coefficients were measured by securing the membrane between two glass cells (Crown Glass) with a rubber gasket. Both cells were filled with phosphate buffered saline (PBS) (0.1 M NaCl, 0.05M phosphate pH 7.4). One cell was sparged with room air (20% $O_2$ assumed) and one side was sparged with HPLC grade He. An oxygen electrode (Microelectrodes) was placed in each cell. The oxygen electrode outputs were connected to a microcomputer controlled data acquisition system and the oxygen concentration from both cells was recorded as a function of time.

Glucose diffusion coefficients were obtained in a similar manner except that one side was filled with 400 mg/dl glucose solution in PBS while the other side was filled with PBS containing no glucose. The concentrations of glucose on both sides of the membranes were measured with a YSI glucose analyzer at 5 minute intervals until equilibrium was obtained.

The curves of concentration vs. time were inputted into a microcomputer and the diffusion coefficients were calculated using the entire curve. Curve fits generally had correlation coefficients ($R^2$) better than 0.95.

Table 1 below shows some of the results for a variety of polymers prepared according to the methods described above.

TABLE 1

Five Representative Polymer Formulations

| Polymer | Diisocyanate | Hydrophilic Diol | Aliphatic Diol | Siloxane |
|---|---|---|---|---|
| 1 | 1-6 Hexamethylene | PEG 600 20% | DEG 60% | Aminopropyl 20% |
| 2 | Isophorone | PEG 600 20% | DEG 50% | Aminopropyl 30% |
| 2 | 1-6 Hexamethylene | PEG 600 50% | None | Aminopropyl 50% |
| 4 | 1-6 Hexamethylene | PEG 400 40% | None | Aminopropyl 60% |
| 5 | 1-6 Hexamethylene | PEG 600 60% | None | Aminopropyl 40% |

Table 2 give some of the physical and chemical properties of the polymers listed above.

TABLE 2

Physical Properties of Representative Polymers

| Polymer | Water Pickup % | D $O_2$ ×$10^{-6}$ cm$^2$/sec | D Glucose ×$10^{-9}$ cm$^2$/sec |
|---|---|---|---|
| 1 | 28.5 | 1.21 | 18.5 |
| 2 | 31.3 | 0.57 | 55.7 |
| 3 | 44 | 1.50 | 105 |
| 4 | 57 | 1.22 | 13.5 |
| 5 | 71 | 1.45 | 155 |

Figure 7A:
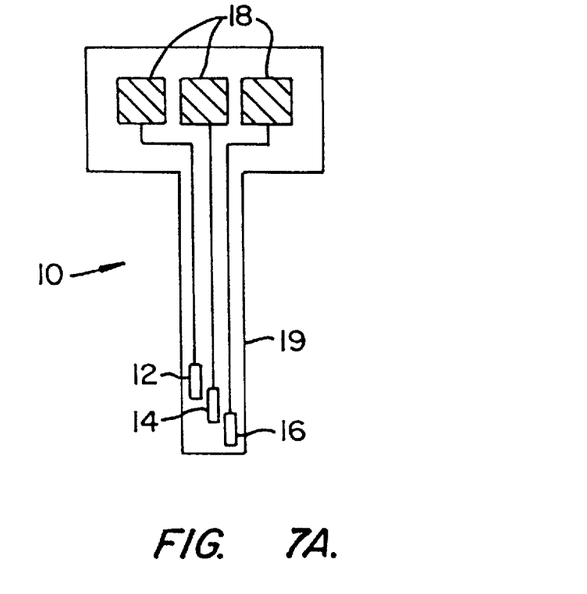
FIG. 7A is a schematic top view of an exemplary glucose sensor having electrodes covered with an exemplary polymer of the present invention.
Figure 7B:
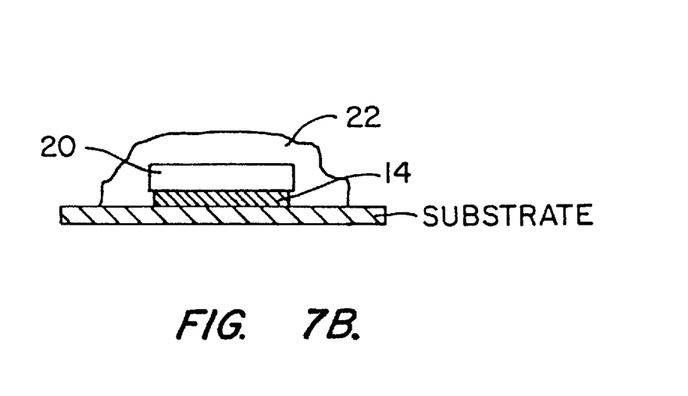
FIG. 7B is a sectional side view of a working electrode covered with layers of enzyme and the polymer composition.

A membrane made from the polymer identified as number 3 above has excellent mechanical properties as well as appropriate oxygen and glucose diffusivities. In order to test this membrane, a prototype glucose sensor generally designated in accompanying drawing FIG. 7A by the reference number 10 was built. The sensor 10 contains a reference electrode 12, a working electrode 14, and a counter electrode 16 deposited on a polymeric sheet 19. A series of bonding pads 18 complete the sensor 10. As shown in FIG. 7B, the working electrode 14 was covered with a layer 20 of the enzyme glucose oxidase and the entire electrode array was coated with a layer 22 of the polymer by dip coating two times from a 5 wt % solution of the polymer in THF. The sensor was connected to a commercial potentiostat (BAS Instruments) (not shown) and operated with a potential of +0.6 volts between the working electrode and the reference electrode.

Figure 8:
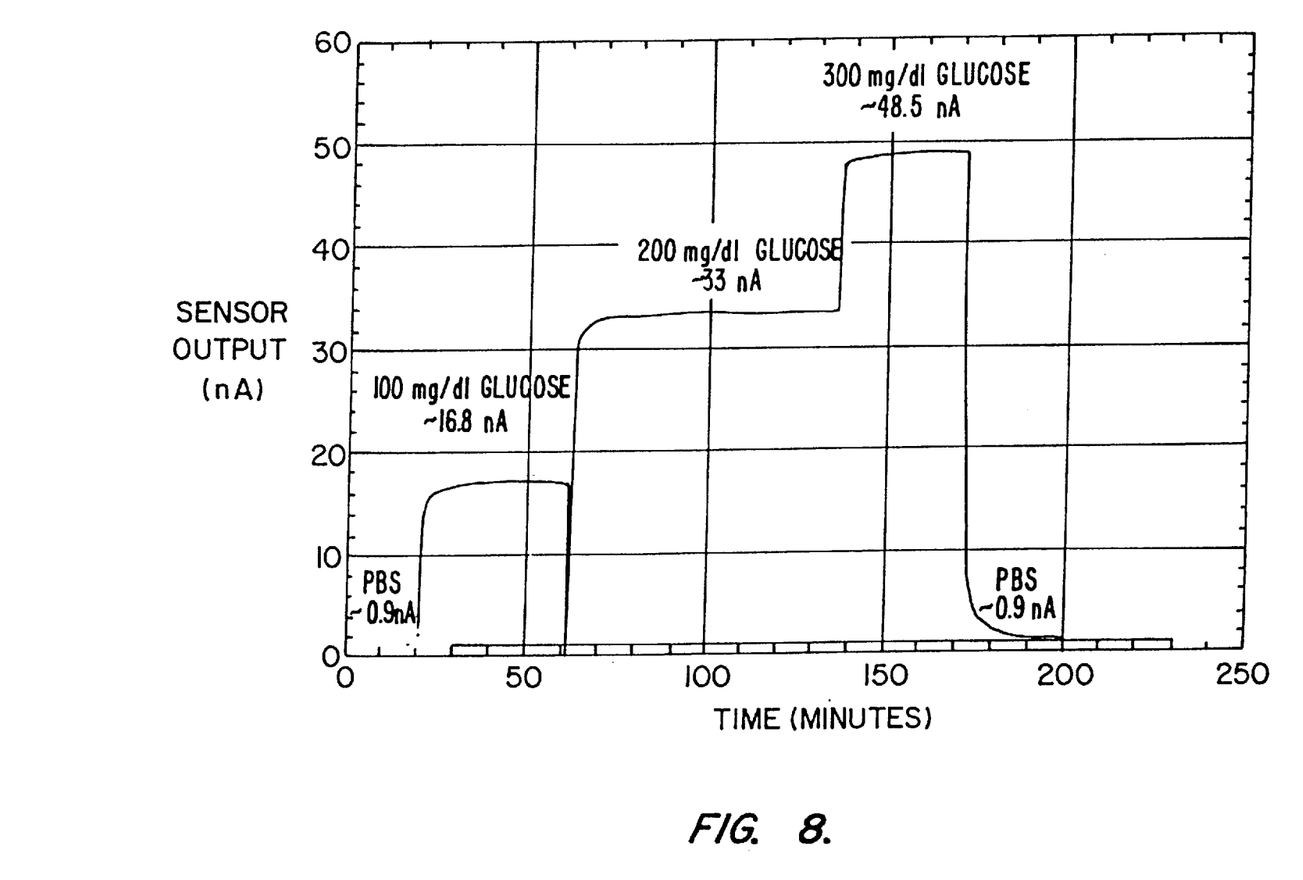
FIG. 8 is a graph showing sensor output in various glucose solutions as a measure of time.

Glucose response is shown in FIG. 8. As seen in FIG. 8, the response of the electrode system is linear over the physiological glucose range, suggesting relative independence of local $O_2$ concentration. All of the other polymers tested show similar behavior to the polymer identified as number 3 shown in FIG. 8 and are acceptable as membranes for biosensor applications. While the principles of the invention may be used in the fabrication of membranes for glucose sensors, the invention is not as limited. Indeed, the membrane in accordance with the invention may be used for the detection of a large number of analytes.

Although a particular embodiment of the invention has been described in detail for purposes of illustration, various modifications may be made without departing from the spirit and scope of the invention. Accordingly, the invention is not to be limited, except as by the appended claims.

What is claimed is:

1. An implantable biosensor for measuring the reaction of an analyte and oxygen, said biosensor having a biocompatible membrane for controlling the permeability of analyte and oxygen to the biosensor elements, said membrane comprising a homogenous polymer composition comprising the reaction products of at least one diisocyanate, at least one hydrophilic diol or diamine, and at least one silicone material.

2. The biosensor of claim 1, wherein the analyte comprises glucose.

3. The homogenous polymer composition of claim 1, further comprising at least one aliphatic diol or diamine added to the reaction.

4. The biosensor of claim 3, wherein the polymer comprises from about 50 mole percent diisocyanate, about 5 to about 45 mole percent hydrophilic diol or diamine, about 5 to about 45 mole percent aliphatic diol or diamine, and about 5–40 mole percent silicone material.

5. An implantable biosensor according to claim 1, wherein said polymer composition comprises at least one diisocyanate selected from the group consisting of hexamethylene diisocyanate, isophorone diisocyanate, 4,4'-methylenebis (cyclohexyl isocyanate) and an aromatic diisocyanate.

6. A homogeneous polymer composition in accordance with claim 3, wherein the aliphatic diol is selected from the group consisting of ethylene glycol, propylene glycol and 1,3 propane diol and the diamine is 1,3 diaminopropane.

7. An implantable biosensor according to claim 1, wherein said polymer composition comprises at least one silicone material selected from the group consisting of a polydimethyl siloxane polymer, a generic bifunctional terminated siloxane, an aminopropyl dimethyl terminated siloxane, a carboxypropyldimethyl terminated siloxane and a carbinol terminated siloxane.

\* \* \* \* \*